(12) United States Patent
Possover

(10) Patent No.: US 11,154,708 B2
(45) Date of Patent: Oct. 26, 2021

(54) IMPLANTABLE NEUROSTIMULATOR AND METHODS FOR IMPLANTING AND USING SAME

(71) Applicant: Marc Possover, Hagendorn (CH)

(72) Inventor: Marc Possover, Hagendorn (CH)

(*) Notice: Subject to any disclaimer, the term of this patent is extended or adjusted under 35 U.S.C. 154(b) by 129 days.

(21) Appl. No.: 16/228,991

(22) Filed: Dec. 21, 2018

(65) Prior Publication Data

US 2019/0192851 A1  Jun. 27, 2019

Related U.S. Application Data

(60) Provisional application No. 62/609,923, filed on Dec. 22, 2017.

(30) Foreign Application Priority Data

Dec. 22, 2017 (WO) .................. PCT/EP2017/084436

(51) Int. Cl.
*A61N 1/36* (2006.01)
*A61N 1/375* (2006.01)
*A61N 1/05* (2006.01)

(52) U.S. Cl.
CPC ..... *A61N 1/36003* (2013.01); *A61N 1/37518* (2017.08); *A61N 1/0558* (2013.01); *A61N 1/36007* (2013.01); *A61N 1/36062* (2017.08); *A61N 1/36128* (2013.01)

(58) Field of Classification Search
CPC .............. A61N 1/0558; A61N 1/36003; A61N 1/36007; A61N 1/36062; A61N 1/36128; A61N 1/37518; A61N 1/0521
USPC .................... 607/48; 128/898, 899
See application file for complete search history.

(56) References Cited

U.S. PATENT DOCUMENTS

| | | | | |
|---|---|---|---|---|
| 5,941,910 A | * | 8/1999 | Schindler | A61F 2/0059 128/898 |
| 2008/0065167 A1 | * | 3/2008 | Boggs, II | A61N 1/0512 607/39 |
| 2010/0312230 A1 | | 12/2010 | Ullestad et al. | |
| 2011/0265804 A1 | * | 11/2011 | Piskun | A61B 17/34 128/898 |

(Continued)

FOREIGN PATENT DOCUMENTS

| WO | 2008021524 A2 | 2/2008 |
|---|---|---|
| WO | 2017044904 A1 | 3/2017 |

OTHER PUBLICATIONS

International patent application No. PCT/EP2017/084436 dated Jul. 17, 2018.

*Primary Examiner* — Carl H Layno
*Assistant Examiner* — Jane C Kalinock
(74) *Attorney, Agent, or Firm* — Bachman & Lapointe, PC; George Coury

(57) ABSTRACT

A method is provided for preventing muscle atrophy, including the steps of identifying a nerve or nerve plexus which controls a targeted muscle or muscle group; implanting a neurostimulator at the nerve or nerve plexus; and transmitting a signal to the neurostimulator to induce activity in the targeted muscle or muscle group. The nerve or nerve plexus can be a pelvic nerve or nerve plexus. The method can be used to prevent atrophy in numerous settings and patients. Further, a tool and method for using the tool are provided which allow for implantation of a neurostimulator in a much easier, faster and safer procedure.

5 Claims, 11 Drawing Sheets

(56) References Cited

U.S. PATENT DOCUMENTS

2014/0228643 A1\* 8/2014 Possover .............. A61B 1/018
600/160
2014/0228905 A1 8/2014 Bolea \* cited by examiner

IMPLANTABLE NEUROSTIMULATOR AND METHODS FOR IMPLANTING AND USING SAME

CROSS-REFERENCE TO RELATED APPLICATIONS

This application claims the benefit of provisional application Ser. No. 62/609,923, filed Dec. 22, 2017.

BACKGROUND OF THE INVENTION

The invention relates to methods for maintaining and/or restoring muscle condition and function using a fully implantable stimulator.

This method has useful application for preventing atrophy during periods of prolonged inactivity, particularly prolonged inactivity under microgravity which is currently encountered during space missions, and which is expected to be encountered for greater periods as space missions increase in duration.

Space is a dangerous, unfriendly place. Isolated from family and friends, exposed to radiation that could increase your lifetime risk for cancer, a diet high in freeze-dried food, required daily exercise to keep your muscles and bones from deteriorating, a carefully scripted high-tempo work schedule, and confinement with three co-workers picked to travel with you by your boss.

There are several risks NASA is researching for a Mars mission. The risks are grouped into five categories related to the stresses they place on the space traveler: gravity fields, isolation/confinement, hostile/closed environments, space radiation, and distance from Earth.

There are three gravity fields in space and especially on a Mars mission. On the several-month trek between the planets, astronauts are weightless. On the surface of Mars, the astronauts would live and work in approximately one-third of Earth's gravity, and when they return home, they will have to readapt to the gravity we take for granted. Transitioning from one gravity field to another is trickier than it sounds. NASA has learned that without gravity working on the body, the bones lose minerals, with density dropping at over 1% per month. By comparison, the rate of bone loss for elderly men and women on earth is from 1% to 1.5% per year. Even after returning to Earth, the bone loss might not be corrected by rehabilitation, so astronauts could be at greater risk of osteoporosis-related fractures later in life and orthopedic disorders. On Mars, if the astronauts don't exercise and eat properly, they will lose muscle strength, endurance, and experience cardiovascular deconditioning since it does not take effort to float through space.

By analyzing how your body changes in weightlessness and after returning to earth's gravity, protection against these changes for a Mars mission must be developed. Bisphosphonates drugs have shown to be effective in preventing bone loss. Regular exercise has been shown to keep the heart healthy, the bones and muscles strong and may even help with balance and coordination. Exercise is therefore an important part of the daily routine for astronauts aboard the space station to prevent bone (osteoporosis) and muscle loss. On average, astronauts exercise two hours per day. The equipment they use is different than what we use on Earth. Lifting 200 pounds on Earth may be a lot of work. But lifting that same object in space would be much easier. Because of microgravity, it would weigh much less than 200 pounds there. That means exercise equipment needs to be specially designed for use in space so astronauts will receive the workout needed.

Maintaining strong muscles is a big enough challenge on Earth. It is much harder to do in space where there is no gravity. Calf muscles biopsies before flight and after a six month mission on the international space station (ISS) show that even when crew members did aerobic exercise five hours per week and resistance exercise three to six days per week, muscle volume and peak power both still decrease significantly. Overall, the data suggests that current exercise countermeasures are not enough. The addition of a second treadmill and the Advanced Resistive Exercise Device (ARED) along with more rigorous exercise regimens are providing good results in preventing muscle loss and preserving overall muscle health—but these steps take a lot of time and effort by astronauts.

New studies are currently ongoing to investigate the efficacy of new exercise devices on ISS, as they provide high resistance and contractions over a wide range of motion that mimic the range and gravity occurring in Earth's environment.

Both astronauts and people with spinal cord injuries (SCI) have difficulties with osteoporosis and muscle loss because of microgravity and immobilization. The present application focuses on prevention and/or treatment secondary to paraplegia and recovery of voluntary leg function in paraplegics, but the disclosed findings can be extrapolated to apply to astronauts.

Severe muscle atrophy occurs rapidly following traumatic SCI. After SCI, there is a rapid and dramatic loss of muscle mass below the level of the lesion that contributes to the development of secondary impairments in individuals with a spinal cord injury. Pressure sores, fractures and deep vein thrombosis are all thought to be at least partially related to musculoskeletal atrophy and disuse in these individuals. Reductions in muscle mass can result in a decreased metabolic rate and increased fat storage if energy intake is not adequately adjusted relative to energy expenditure. Paraplegics unable to bear weight on their limbs are not exposed to forces to stimulate bone formation. The loss of mechanical stimuli to the bone is considered a powerful influence in sustaining bone integrity. Immobility leads to a changing pattern of loading in the paralyzed areas, which respond by alteration in skeletal structure and an increased risk of fractures. The fracture rate in the SCI population has been reported to be from 1% to 21% of patients. Fracture prevalence has been reported to increase with time post-SCI; from 1% in the first 12 months to 4.6% in individuals 20 years post injury. Fractures are more likely to occur in individuals with lower than with upper motor neuron lesions, and they are more likely in individuals with complete injuries than incomplete injuries. By far the most common sites for fracture after SCI are the distal femur and the proximal tibia. In general, hip bone mass density (BMD) declines rapidly for the first several months, and then declines more slowly until reaching equilibrium at 12 to 16 months post injury. Lumbar spine BMD generally does not decline and may even increase after SCI.

Functional electrical stimulation (FES) is potentially useful in the rehabilitation of patients with SCI. Claimed benefits include improvement of contractures, neurogenic osteoporosis, deep vein thrombosis, and edema, as well as amelioration of spasticity. 12 weeks of neuromuscular electrical stimulation-induced RET elicited substantial hypertrophy in subjects with long-term SCI. These results provide further evidence to the responsiveness of skeletal muscle to RET in the SCI population. Large increases in skeletal muscle size are possible, provided the appropriate mode of exercise is used; large increases in skeletal muscle size are possible even years after injury if the appropriate mode and intensity of exercise are utilized.

Because improving physical fitness decreases cardiovascular disease risk and muscle atrophy, a substantial amount of recent research has attempted to incorporate exercise training in the treatment program for patients with SCI in attempts to improve functional capacity and ameliorate muscle wasting. The majority of research involving exercise training in patients with SCI has incorporated leg exercise with functional electrical stimulation (FES) and has shown increases in muscle endurance and strength.

Functional electrical stimulation can be used to produce isometric contractions, to facilitate gait, or to produce contractions against resistance during cycling or leg extensions in individuals with SCI. Despite variability in the intensity, duration, and frequency of the exercise interventions, the positive effects of FES exercise on muscle are fairly well established.

FES muscle strengthening before FES cycle ergometry may also be advantageous for increasing muscle. An FES training program that began with quadriceps strengthening and progressed to concurrent arm ergometry and FES cycle ergometry produced significant increases in muscle cross-sectional areas (rectus femoris ↑31%, sartorius ↑22%, adductor magnus-hamstrings ↑39%, and vastus medialis-intermedius ↑31%). In fact, the muscle-strengthening component may have the greatest impact: significant increases in quadriceps muscle protein synthetic rate were noted in 4 men with paraplegia after 10 weeks of quadriceps muscle strengthening, but the increase in muscle area after transition to a cycle ergometry program was not significantly different from the end of the first regimen.

In studies on the effect; of prolonged microgravity or immobilization muscular atrophy can be prevented or attenuated if FES is initiated early, prior to the development of extensive atrophy and degeneration.

The magnitude of bone lost in the lower limbs following SCI is substantial and has been described in a number of cross-sectional studies using both DXA and pQCT. Hip-DXA was analyzed using DXA. There is evidence that the nervous system participates in skeletal development and bone turnover. Clinical studies also indicated that neurological injuries are associated with the development of a rapid and severe osteoporosis that is not only due to a compromised biomechanical function but can have a central nervous system origin. All paraplegics were in a chronic stage, which suggests that not only the mechanical (forces-standing), but the neurogenic factor seems to co-exist as an influential regulator in osteoporosis during years of paralysis. The recent scientific finding of a sympathetic innervation of bone tissue and its role in the regulation of bone remodeling, is of major interest in situations where uncoupling between osteoclasts and osteoblasts occurs. Today there is clinical evidence that the sympathetic regulation of bone does exist in humans and plays a clinically important role in diseases characterized by excessive sympathetic activity. Also, changes in the autonomic nervous system are proposed to cause attrition of SCI bone, via changes in vascular tone and flow. Sympathetic denervation in SCI may cause arteriovenous shunts and a slowdown of intraosseous blood flow, thus increasing bone resorption. Reduced peripheral sympathetic nervous system activity in individuals with SCI may also contribute to reductions in resting metabolic rate. Loading is associated with ambulation and normal physical function is critical to maintaining both trabecular connectivity and bone mineral mass.

Studies of skeletal changes associated with weight bearing activities after SCI are also limited. After 12 to 20 weeks of training with an ambulation device that combined FES and a modified walker, no significant increase in BMD was observed. Early weight bearing after acute SCI by standing or treadmill walking (5 times weekly for 25 weeks) resulted in no loss or only moderate loss in trabecular bone compared with immobilized subjects.

It has also been shown that isometric contraction of voluntary muscles may cause an increase in blood pressure that may not be dependent on the specific muscle used.

Functional electrical stimulation applied to the lower extremities of tetraplegia patients has been shown to have predictable effects on the hemodynamic responses to orthostatic challenge. Functional electrical stimulation to assist lower extremity resistance training exercise has been used extensively for the purpose of improving or maintaining cardiovascular fitness in persons with SCI without specific attention to its possible effect on blood pressure. Research had documented evidence that applying FES to the quadriceps of patients with SCI above T6 resulted in a reproducible elevation in blood pressure during the stimulation. Sampson suggests that the observed response is not caused by increased venous return secondary to the muscle-pump or a hypertensive reflex response to an isometric muscle contraction, but rather may simply be a result of the (noxious) stimulus itself causing an autonomic dysreflexia-type reflex sympathetic reaction. This is supported by the relative bradycardia and hypertension seen when the subjects were stimulated while horizontal compared with those receiving no electrical stimulation.

There is a long history for the therapeutic use of electrical stimulation. More than 30 years ago functional electrical stimulation (FES) was developed as an orthotic system to be used for SCI patients. The goal of FES is to obtain an immediate contraction of the skeletal muscles that will lead to a functional movement. Even though FES assisted walking has been available for more than three decades, it has not been widely used in rehabilitation because the stimulators were bulky, unreliable, prone to breakage and expensive. Classical FES being based on stimulation of the muscles directly using "epimysial" implanted electrodes or transcutaneously using surface pads.

The situation began to change with the introduction of laparoscopy to the world of the pelvic nerves. Advances in video endoscopy enable good access to the retroperitoneal pelvic space, providing the necessary image quality with magnification of the structures and appropriate instruments for adequate procedures like nerve decompression and neurolysis. Laparoscopy is also the only technique that enables selective placement of electrodes to all pelvic nerves and plexuses.

Nerve stimulation induces a harmonious and controllable contraction of the entire muscle while epimysial/percutaneous stimulation induces an on/off contraction of the muscle (an electrical-induced cramp of the muscle). This in turn makes such contraction difficult to be used in everyday life and also causes a high degree of muscle fatigue.

Laparoscopy offers patients an "in-body FES"; this technique, called the LION procedure (Laparoscopic Implantation Of Neuroprothesis) applied to the pelvic somatic nerves may be used for restoring voluntary control of locomotion in complete motor paraplegia. In more recent studies, we have moreover demonstrated that pelvic nerve stimulation might induce changes that affect the central nervous system to engage residual spinal and peripheral pathways for recovery of voluntary motion of the legs in chronic paraplegics secondary to spinal cord injuries.

Each of the above areas indicates a situation wherein methods according to the present invention can advantageously be used to address specific issues.

Because of a growing interest from the medical community for these new advances in pelvic neurofunctional surgery, the International Society of Neuropelveology (ISoN) (www.theison.org) was founded in 2014 to provide universal access to education in this area.

The LION-procedure to the pelvic somatic nerves (sciatic+femoral nerves) is a minimally invasive surgical procedure that consists of the implantation the laparoscopic way of microelectrode(s) to the targeted nerves for electrical stimulation or neuromodulation. The laparoscopic approach enables an easy and minimally invasive approach to the pelvic nerves for the placement of neurostimulators to the pelvic somatic nerves. Deep within the pelvic cavity, the neurostimulators are protected from external trauma, device breakage and migration. The mean duration of such a LION procedure in-patient with normal BMi is <1 hour. Locomotor training can be started directly after implantation.

Therefore, the LION procedure enables continuous nonstop FES of the pelvic nerves, avoiding all disadvantages of previous FES-techniques of transcutaneous or epimysial (direct stimulation of the muscle) electrical stimulation.

Because direct nerve stimulation requires much less energy than with past techniques, efforts have been made over the last 10 years toward miniaturization of neuroprothesis.

In paraplegics, we currently use rechargeable neurostimulators, but the required energy for non-paraplegics is much lower and therefore "normal" batteries with a 7-10 years lifespan would likely be sufficient.

SUMMARY OF THE INVENTION

In accordance with the present invention, the foregoing issues have been readily addressed.

Specifically, methods are provided whereby persons with injury can be helped in avoiding muscle atrophy and thereby maintaining better health. Further, methods are provided whereby persons who are in long periods of inactivity can nevertheless avoid muscle atrophy, and this applies equally to environments where such individuals might also be subjected to long periods of microgravity conditions. Thus, these methods have direct applicability to long duration expeditions into space, such as for example travel to Mars.

Still further, the methods of the present invention have applicability to persons looking to fight the effects of aging in general, even without any of the special conditions such as injury and/or long periods of inactivity or lack of gravity, as mentioned above.

In accordance with another aspect of the invention, a tool and associated method are provided whereby electrodes and in some cases electrodes and accompanying pacemakers can be implanted to a patient in the endo pelvic region with greatly reduced trauma to the patient, as well as reduced risk of infection.

According to the invention, one method is provided for preventing muscle atrophy, wherein the method comprises the steps of identifying a nerve or nerve plexus which controls a targeted muscle or muscle group; implanting a neurostimulator at the nerve or nerve plexus; and transmitting a signal to the neurostimulator to induce activity in the targeted muscle or muscle group. This is preferably within the pelvic area, specifically a pelvic nerve or nerve plexus. On the other hand, it is within the broad scope of the invention to apply the method in other areas as well, for example to the nerves of the trunk and/or upper limbs, for example to restore movement or induce muscle working of the hand or arm.

Because the neurostimulator is implanted within the body, for example within the pelvis, training of the muscles of the buttocks, the back and of the lower extremities can be achieved by stimulation of the pelvic somatic nerves. Continuous pelvic nerve stimulation with low current electricity (lower value for the first minimal skeletal muscle contraction) is absolutely not painful, and could be used for example to provide astronauts with continuous muscle training without the need of active participation of the person who can at same time absolve some other activities. This training can also be continued during the night, when the astronaut is in a deep sleep.

In parallel, further programs are installed to train the quadriceps muscles, one for each leg, and one for both legs together. When stimulation parameters are fixed by a pulse width at 60 µs, a frequency at 300 Hz (with variable intensities), harmonious full extension of the knees is obtained, independently from voluntary control of the patient or subject, and without any pain (electrical stimulation is felt as a gentle tingling while the skin becomes warm due to an increase blood supply). This "training-stimulation-program" can be combined with the usual muscle training program in space, if required. Locomotor training and stimulation of the pelvic nerves with both isometric and eccentric gluteal muscle contractions induces an increase of gluteal muscle mass ("gluteal pads effect"). Such a passive "e-training" may considerably reduce the intensity of body training required in the current conditions on the ISS, allowing more time for the astronauts to rest and work.

Of course, it should be appreciate that the above methods can find use in numerous other environments such as in treatment of patients with SCI or other injuries and/or paralysis, or even with patients or subjects who are looking to simply fight the effects of aging.

The invention also finds use in the prevention/treatment of decubitus lesion if immobilization is required. Because sympathetic trunks travel downward outside the spinal cord and first anastomose to the sacral plexus, sciatic nerve stimulation permits neuromodulation of the sympathetic nervous system of the lower extremities and of the bottom. This low frequency/low voltage stimulation of the pelvic sympathetic nerves induces a peripheral cutaneous vasodilatation resulting in a powerful decubitus prophylaxis. In vivo studies involving animal models have even revealed that electric stimulation of wound healing processes results in more collagen deposition, enhanced angiogenesis, greater wound tensile strength, and a faster wound contraction rate. In addition, electric stimulation has been shown to improve tissue perfusion and reduce edema formation that results in a significant increase in transcutaneous oxygen pressures.

The present invention also finds use in the prevention/treatment of osteoporosis. Because of evidence of the role of the sympathetic innervation of bone tissue and its role in the regulation of bone re-modelling in humans, muscle training (pressure applied to the bones due to the muscles contraction) and sympathetic nerve stimulation offer a treatment and prophylaxis of osteoporosis not only for people in space, but for the general population.

In further accordance with the invention, methods are provided which help to prevent secondary complications of osteoporosis, such as cardiovascular failure or formation of kidney stones.

Use in addressing osteoporosis and related adverse conditions is further supported by additional information generated by personnel from space shuttle flights. Peggy Whitson, a NASA astronaut and biochemist, has said that even those who went on short 18 day space shuttle flights had been found to be affected by osteoporosis. During space flight, crew members lose bone density. "And the calcium that is released probably ends up in the urine. Higher calcium levels are probably contributing to increased calcium-stone forming potential. Stones can usually be passed, painfully, without surgery. Drinking plenty of water both helps pass the stones, and prevents them forming. But, experts say urinating in space can be difficult. Peggy Whitson added: "Urinating in toilets in orbit is time consuming, crew members are very busy, and if they do extra-vehicular activity they don't have the option. Vomiting because of motion sickness can also lead to loss of fluids.

Kidney stones could prove to be the "final frontier" that astronauts embarking on long distance missions have to tackle. Scientists say they must find ways of preventing space travelers from developing the stones on long trips, such as missions to Mars. Affected astronauts could become incapacitated, potentially leading to missions being aborted. Kidney stones can form anywhere within the kidney or bladder and range from tiny microscopic crystals to stones as large as walnuts. They can move from the kidney towards the bladder causing a number of problems including excruciating pain. If the stone completely blocks the tube draining the kidney, the kidney could stop functioning altogether. Development of a kidney stone on a mission to Mars could be catastrophic.

Because of evidence of the role of the sympathetic innervation of bone tissue and its role in the regulation of bone remodelling in humans, muscle training (pressure applied to the bones due to the muscles contraction) and sympathetic nerves stimulation (e.g. in the sciatic nerves) offer a treatment and prophylaxis of osteoporosis in people in space.

In another aspect of the invention, methods are provided which can control the aging process. Muscle atrophy induces a "free space" for adipocytes that in turn further increase the muscle atrophy. Adipocytes produce leptin, interleukin that in turn also increase muscle atrophy. Muscle strength gradually decreases from the $30^{th}$ year until about the $50^{th}$ year of life. In the $6^{th}$ decade of life, an accelerated, non-linear decrease by 15% has been observed, and by the $8^{th}$ decade, this may be up to 30%. This additionally results in a substantial impairment in the sensorimotor information exchange, with a reduction in the quality of inter-muscular and intramuscular coordination. Functional losses in strength and balance capacity, and increasing gait uncertainties are the result. The risk of acute problems owing to falls and injuries and chronic recurrent and degenerative illnesses rises.

Prevention of the ageing process mainly focuses on the control and treatment of muscle atrophy. Several therapies have been proposed for preventing the ageing process such as mental activity, muscle training, and high-protein diet. A crucial factor in this is sustaining a high individual strength capacity. The elderly need strength training more and more as they grow older to stay mobile for their everyday activities. The goal of training is to reduce the loss of muscle mass and the resulting loss of motor function.

In spite of losing its elasticity, aging muscle tissue is able to resist mechanical stretching of the muscle, especially in eccentric exercise. With this in mind, targeted, negative-dynamic training (such as brake load, weight transfer) is considered crucial. Especially intramuscular and inter-muscular coordination skills can be trained in this manner. Furthermore, the cardio-circulatory and metabolic strain is lower than for concentric and isometric exercise. Several studies have shown that strength (resistance) training can counteract age related impairment. The crucial factor in maintaining strength capacity is an increase in muscle mass. Progressive strength training in the elderly is efficient, even with higher intensities, to reduce sarcopenia, and to retain motor function.

Therefore, the goal of training is to reduce the loss of muscle mass and the resulting loss of motor function. The stimulation of the muscles of the lower extremities definitively prevents the ageing process, and also helps to prevent further complication such as destabilization of the skeleton with increased orthopedic complications. The LION procedure to the pelvic somatic nerves (sciatic and femoral nerves) enables a continuous low-level stimulation of the muscles of the lower extremities and of the bottom as a passive but extremely efficient strength training for prevention or even treatment of muscle atrophy as a major factor responsible for sarcopenia. Thus, the LION procedure to the somatic pelvic nerve can be considered as an anti-aging treatment.

Stimulation of the pelvic nerves for muscle training is especially appropriate in elderly people who are not capable of active muscle training because of pain, motoric limitations, or subcortical pathologies (dementia, comatose patients, Parkinson, etc.).

It should be appreciated that the present invention and methods, with the capability of implantation micro stimulators within the body to nerves for muscle stimulation, opens the door to a whole new area of humanity, the "e-control-body", in which implanted electronics may help the human body to better performance and a longer life as a result.

BRIEF DESCRIPTION OF THE DRAWINGS

A detailed description of preferred embodiments follows, with reference to the attached drawings.

DETAILED DESCRIPTION

The invention relates to methods using laparoscopically implanted neurotransmitters to stimulate a nerve or nerve plexus and thereby cause muscle movements and/or contractions which can exercise the muscle and thereby prevent muscle atrophy and other adverse conditions. This method has use in numerous settings, including prevention of muscle atrophy in individuals who must endure long periods of inactivity, for example during long missions in space; prevention of muscle atrophy and decubitus in individuals who have injuries such as SCI which prevent movement; and also as a prophylactic against aging in any other conditions. Such methods also are believed to prevent osteoporosis and adverse conditions accompanying osteoporosis, again in similar settings as set forth above. For an individual on a prolonged mission in space or other microgravity environment, the present method not only prevents muscle atrophy, but also prevents bone loss or osteoporosis, which is also believed to potentially cause kidney stones.

In a further aspect of the invention, a tool is provided for implantation of neurostimulators for use according to the invention, and a method is provided, using this tool, for greatly improving the overall implantation process, and making the process easier, faster and safer. These methods and tool are related to an invention by the same applicant which is disclosed in PCT/EP2017/084436, filed Dec. 22, 2017, which is incorporated herein by reference as if set forth herein in its entirety.

Advances in the structure of neurostimulators, which are also referred to herein as microstimulators and/or electrostimulators, have made new methods of implantation possible, as well as broadening the use of such devices to address numerous potential issues or conditions. Further, the present invention provides an advance in the form of a tool which greatly simplifies the implantation of an electrostimulator, and particularly of a combination of generator or pacemaker and a neurostimulator to desired locations within the body.

Figure 1:
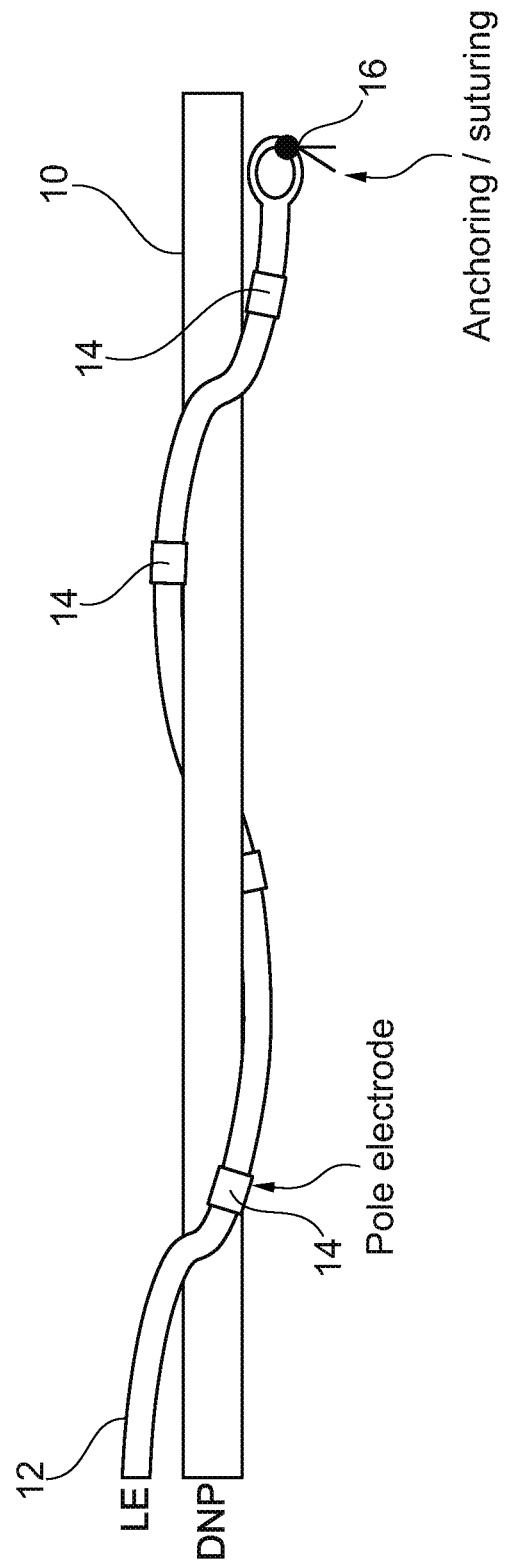
FIG. 1 schematically illustrates the implantation of a micro neurostimulator to a suitable nerve or nerve plexus.

FIG. 1 illustrates one method of connecting an electrode to a target nerve, in this case the dorsal nerve of the penis, or DNP 10. As shown, the neurostimulator 12 can be provided as an elongate flexible structure with a series of pole electrodes 14 arranged along the length of the neurostimulator 12. As shown, neurostimulator 12 can advantageously be wrapped around DNP 10 with pole electrodes 14 in contact with DNP 10 as desired, and with an anchoring or suturing structure 16 to secure an end of the neurostimulator 12 in place. Using a laparoscopic implantation method, pole electrodes 14 can be arranged around DNP 10 as shown to ensure good functional contact.

Figure 2:
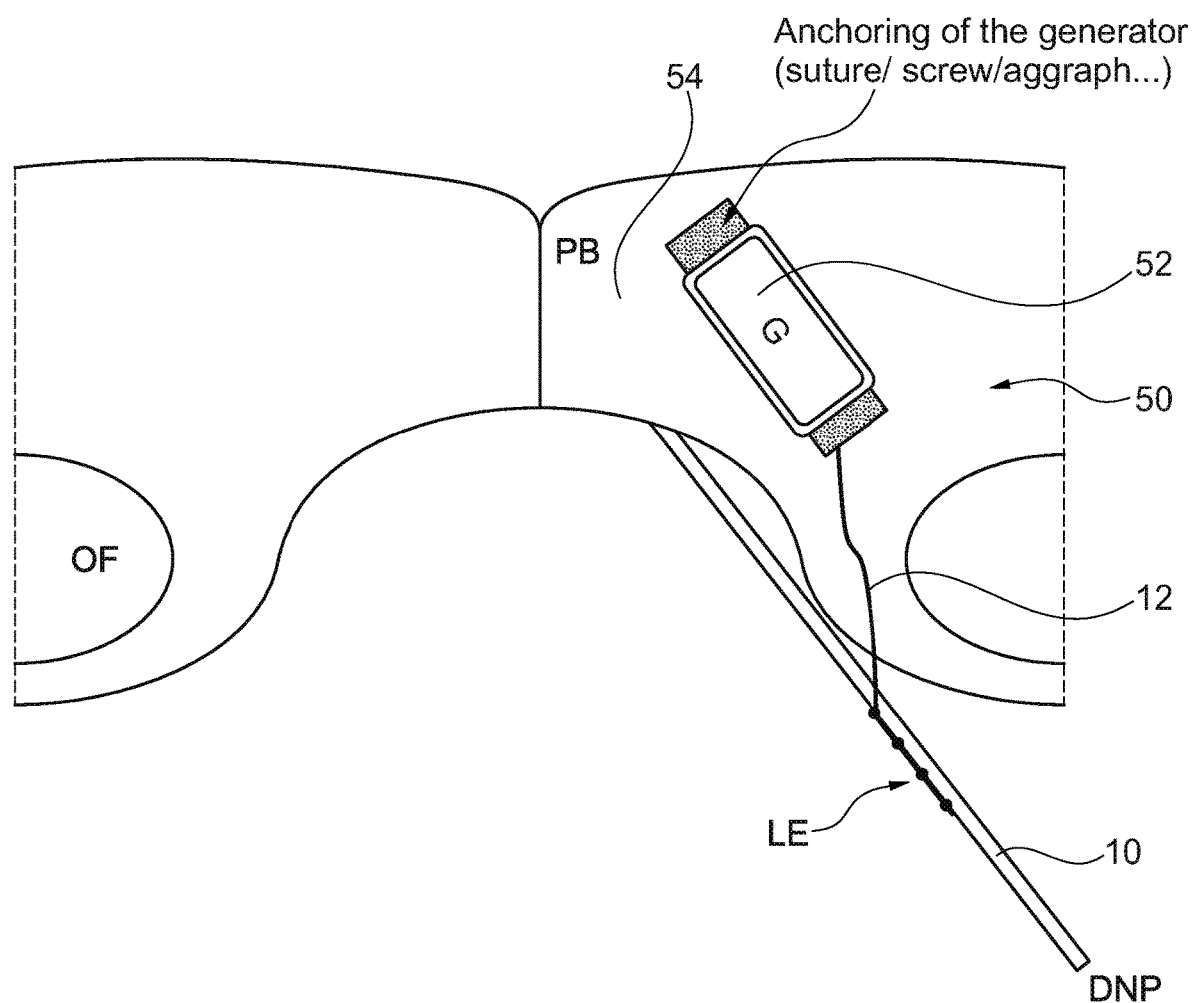
FIG. 2 further schematically illustrates implantation and includes illustration of the generator for the stimulator.

FIG. 2 shows a device 50 including neurostimulator 12 and a generator 52 or pacemaker, which is functionally connected to neurostimulator 12 and issues commands or pulses to neurostimulator 12 to interact with a target nerve as desired. As shown, while neurostimulator 12 is anchored to DNP 10 as also shown in FIG. 1, generator 52 is anchored to a secure location, in this case to the pubic bone 54 within the pelvis or endopelvic region of the patient. Generator 52 can be anchored in place with a suture, screw or the like.

Figure 3:
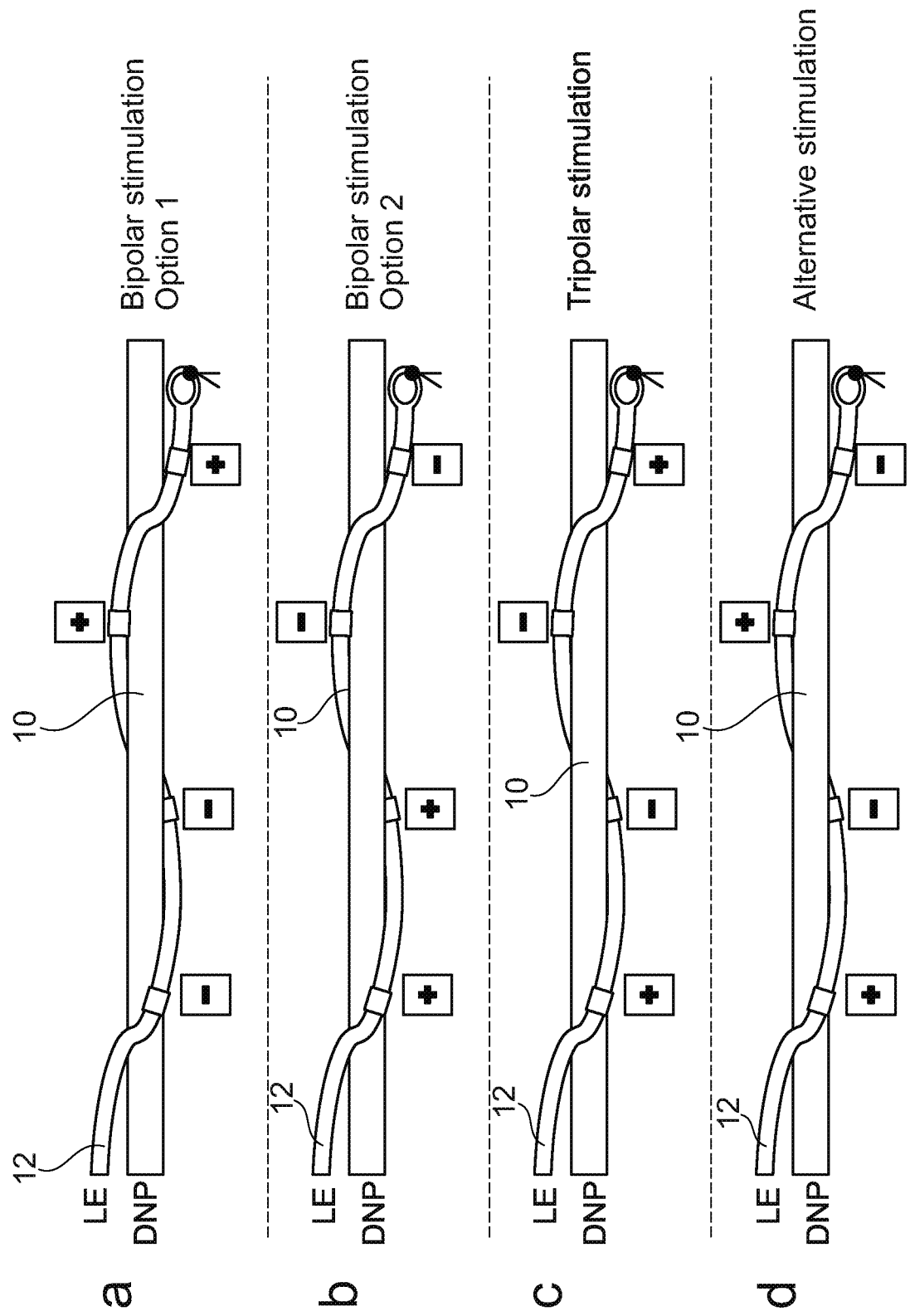
FIG. 3 illustrates alternative implantations to allow different types of stimulation of the target nerve.

FIG. 3 shows a series of different configurations of the implantation of stimulator 12 to DNP 10, with different arrangement of poles to create different types of stimulation of the target nerve. FIG. 3, views a and b, show configurations which result in bipolar stimulation, while view c shows a configuration for tripolar stimulation, and view d shows a configuration for an alternative stimulation different from those produced in views a, b and c.

Figure 4:
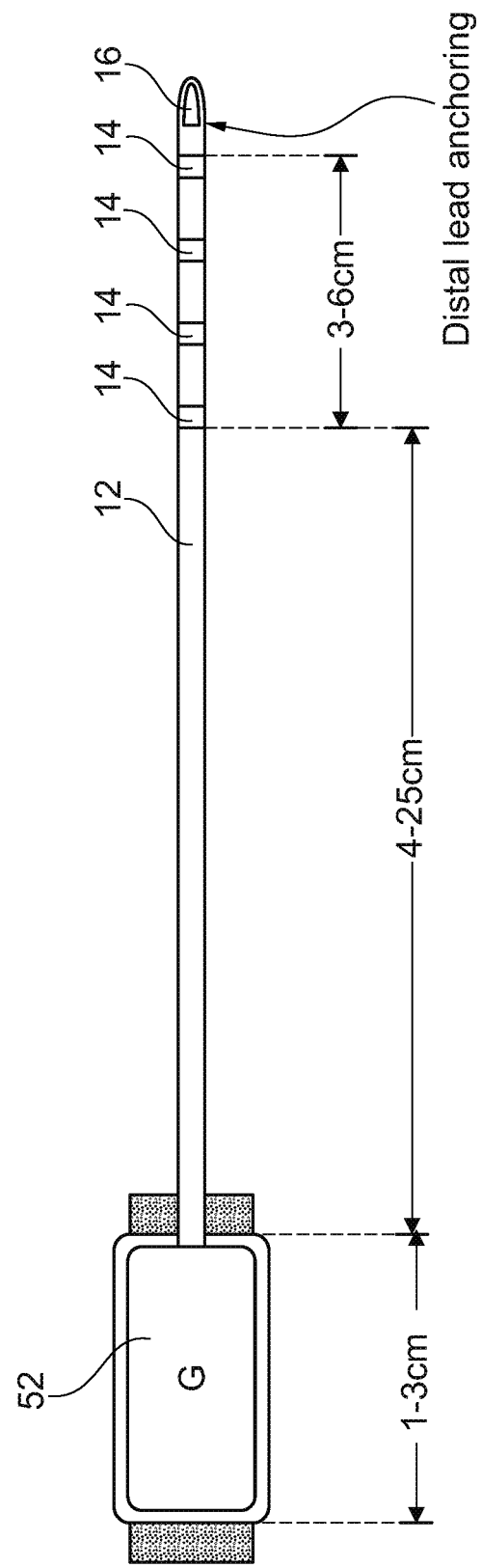
FIG. 4 further illustrates features of the neuro stimulator and generator as a single assembly according to the invention.

FIG. 4 shows a further illustration of neurostimulator 12 with connected generator 52. As shown in this non-limiting embodiment, neurostimulator 12 can be directly attached to generator 52 at one end, and can have a plurality of pole electrodes 14, in this case four pole electrodes 14, positioned along the distal end of the stimulator, and spaced properly to line up with a target nerve plexus. The distal end of stimulator 12 ends in a lead anchoring structure 16 which can be used to secure this end of the neurostimulator in place with the pole electrodes in contact with the target nerve or nerve plexus. It should be noted that the neurostimulator and generator according to the invention can advantageously be used to contact with the pelvic nerve or nerve plexus, within the pelvis of the patient, to allow control of muscle contractions and the like in the buttocks and lower extremities.

As discussed above, while one aspect of the present invention is directed to the benefits of exercising the muscles in this area, for example to prevent atrophy of the targeted muscles and also to give the body the benefit of exercise in preventing osteoporosis, the neurostimulator of the present invention can also be implanted to other areas and other target nerves, some also within the pelvis and others that are in different areas. In connection with the embodiment targeting the DNP within the pelvis, a neurostimulator implanted as described above can be used to exercise the muscles of the buttocks and lower extremities of persons who can benefit from such exercise, including persons on lengthy space missions, persons suffering from traumatic injury such as SCI, and others including athletes, and even virtually anyone looking to prevent some aspects of aging.

In order to obtain these benefits, a person or persons in one of these categories has a nerve or nerve plexus identified which corresponds to a muscle or muscle group which is to be stimulated. The nerve or nerve plexus is then exposed and approached using laparoscopic techniques. The neurostimulator can then be implanted to the targeted nerve or nerve plexus, preferably under observation through one or more laparoscopically deployed imaging apparatus. Once the neurostimulator is implanted, and preferably also the generator for the stimulator, the implantation step is complete and the generator can then be used to cause the stimulator to induce contractions or other movement in the muscles, thus producing the desired effect of fighting muscle atrophy, helping to prevent osteoporosis, and the like. Axial length of the components are relevant since the entire device is to be implanted. Thus, the generator can have a length which is preferably between 1 and 3 cm, while the main portion of electrode 12 can have a length of between 4 and 25 cm, and spacing of pole electrodes 14 can be over a distance of 3-6 cm.

Figure 5:
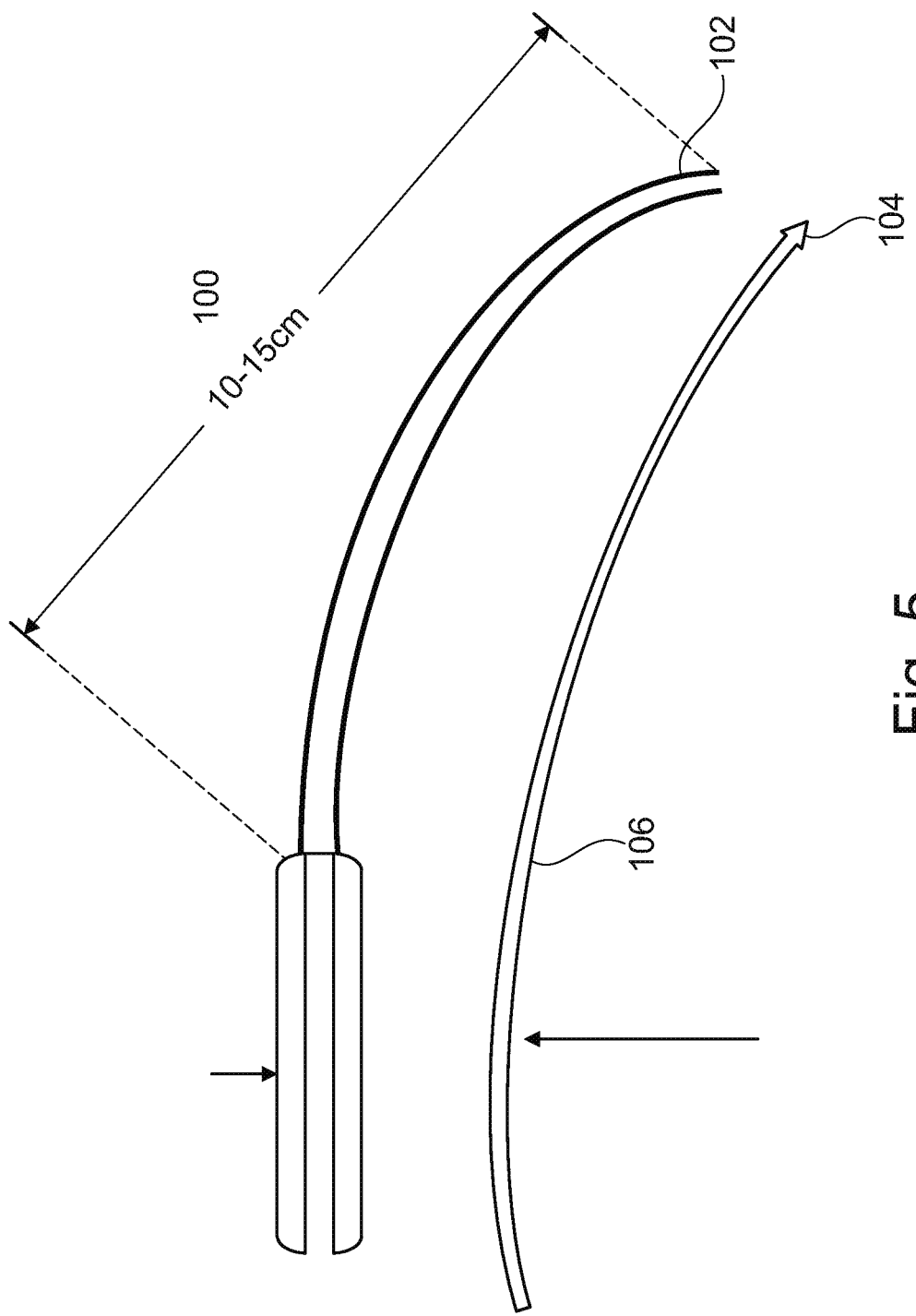
FIG. 5 illustrates a placement tool for use in an aspect of the invention related to a method for implantation.

FIG. 5 illustrates components of a tool 100 which can advantageously be used to implant an electrode as described above. Tool 100 is an elongate tube or other hollow structure which is made from material which is substantially rigid or resilient, and which terminates in a distal end portion 102 which has a curve over a distance of between about 10 and about 15 cm. A sharp tip 104 is removably mounted to end portion 102. In the embodiment illustrated, tip 104 is mounted to the end of a flexible cord or shaft 106 which can be positioned within the hollow tube of tool 100. With sharp tip 104 in place, tool 100 can be used to make a small incision and then extend the end of tool 100 into a desired location in the body of a patient, for example within the pelvis. As will be further described below, sharp tip 104 can then be removed, and the hollow shaft of tool 100 left in place for the next steps of the procedure wherein an electrode is to be implanted.

It is advantageous that tool 100 have a particular length of a curved end portion, that the tool be somewhat rigid, and that a removable sharp tip 104 be provided at the end of tool 100. The structure of tool 100 allows a surgeon to reliably find the location of, for example, the dorsal nerve of the penis or DNP, which can be used to stimulate contractions or other movements of the buttocks and lower extremities.

Figure 6:
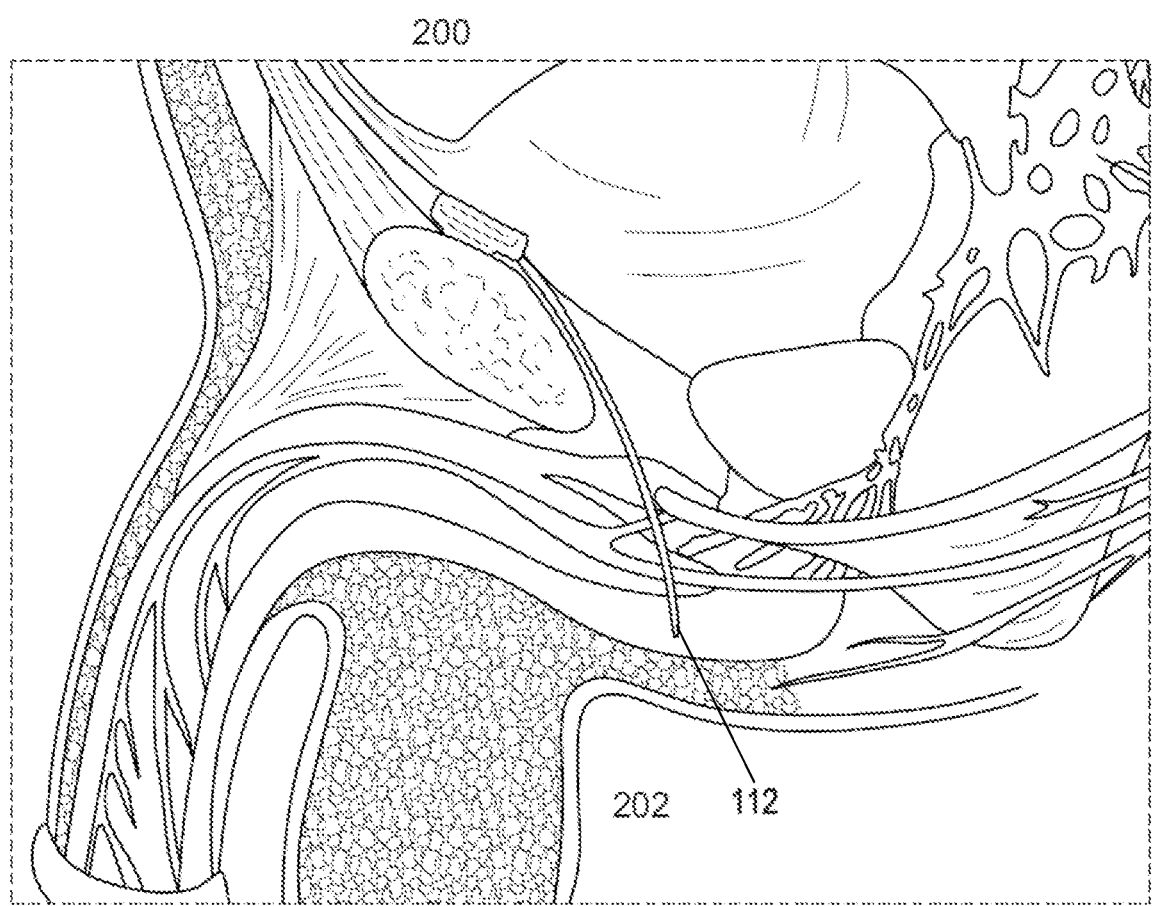
FIG. 6 further illustrates implantation using the tool of FIG. 5.

One advantageous use of tool 100 is in conjunction with other laparoscopic entry to the same location, preferably the pelvis. According to this configuration of the invention, and referring to FIG. 6 (as well as FIGS. 7-11), the first step can be to enter the pelvic area laparoscopically from above the pelvis floor, or from an area in FIG. 6 shown as top 200. After this entry, the pelvic area can be expanded as necessary, and illumination or other video provided to allow the surgeon to see the target area. Then, a tool 100 is used to access the same pelvic area, but from below the pelvis, an area shown in FIG. 6 as bottom 202. Tool 100 is inserted to this area under observation from one or more laparoscopic tools inserted from the top, and once the surgeon can see tool 100, the sharp tip of tool 100 can be removed by the surgeon by introducing a forceps or other manipulating tool through a laparoscopic tube and into the pelvic area to remove the sharp tip from tool 100, leaving only an open tube as illustrated in the upper view of FIG. 5.

At this stage, a combination generator and electrode can be introduced into the pelvic area from the top, through a laparoscopic entry, to first mount the generator against the inner side of the pelvic bone as shown. Then, the distal end of the electrode can be fed to the open end of tool 100, which can then be removed and during this removal, the end of electrode 112 is properly positioned across the target nerve.

Figure 7:
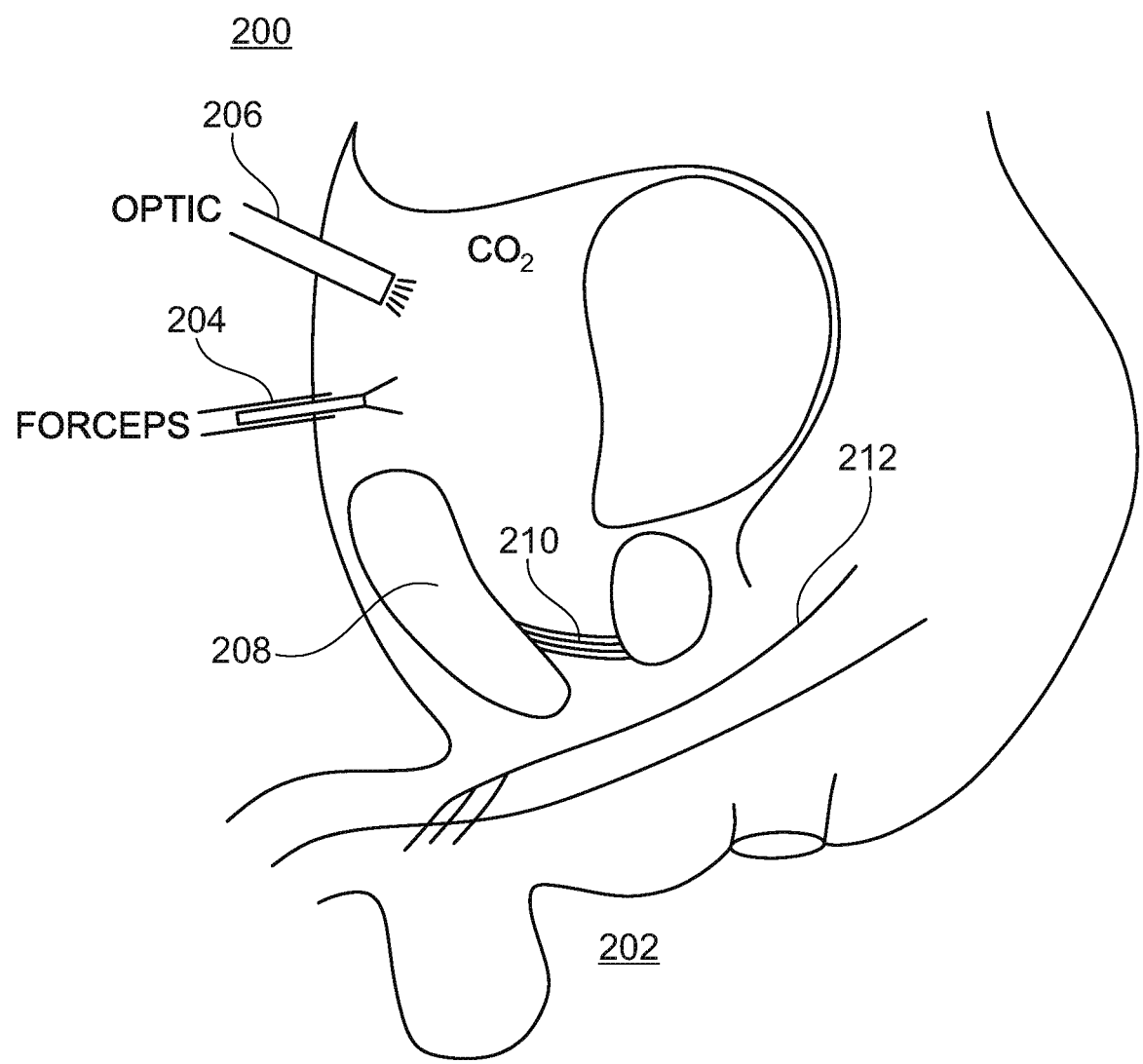
FIGS. 7-11 illustrate the steps of a method for implanation in accordance with one aspect of the present invention.

FIG. 7 shows the relevant anatomy in the pelvic area wherein a process in accordance with the present invention is to be conducted.

In the first step which is illustrated in FIG. 7, an endoscopic dissection of the Retzius space is made, approaching either trans or retroperitoneally. Such an approach is illustrated in FIG. 7, for example with the access of forceps 204 and optics 206. Also as indicated, $CO_2$ can be injected into this space to inflate the cavity and allow better access and viewing of important details. It should also be appreciated that, in FIG. 7, the pubic bone is illustrated at 208, the pelvic floor is illustrated at 210 and a representative nerve which could be the target of the procedure is illustrated at 212.

Figure 8:
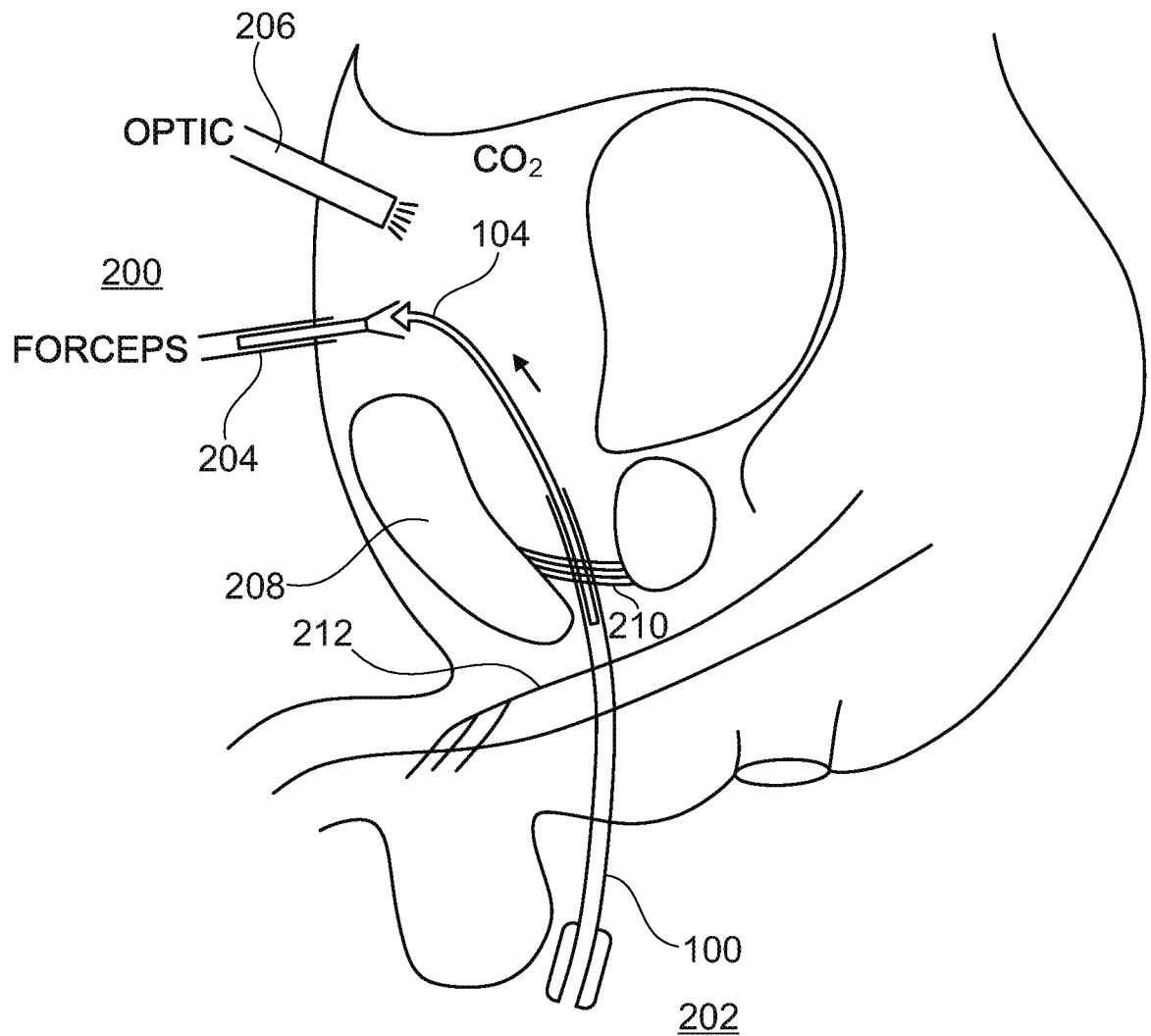

Referring to FIG. 8, the next step of the process is to introduce a tool 100 with sharp tip 104 from below the pelvic floor 210 and into the endoscopically accessed space to the extent that tip 104 can be seen through optics 206. At this stage, forceps 204 are used to grasp tip 104 and remove tip 104 endoscopically, for example through a cannula accommodating forceps 204.

Figure 9:
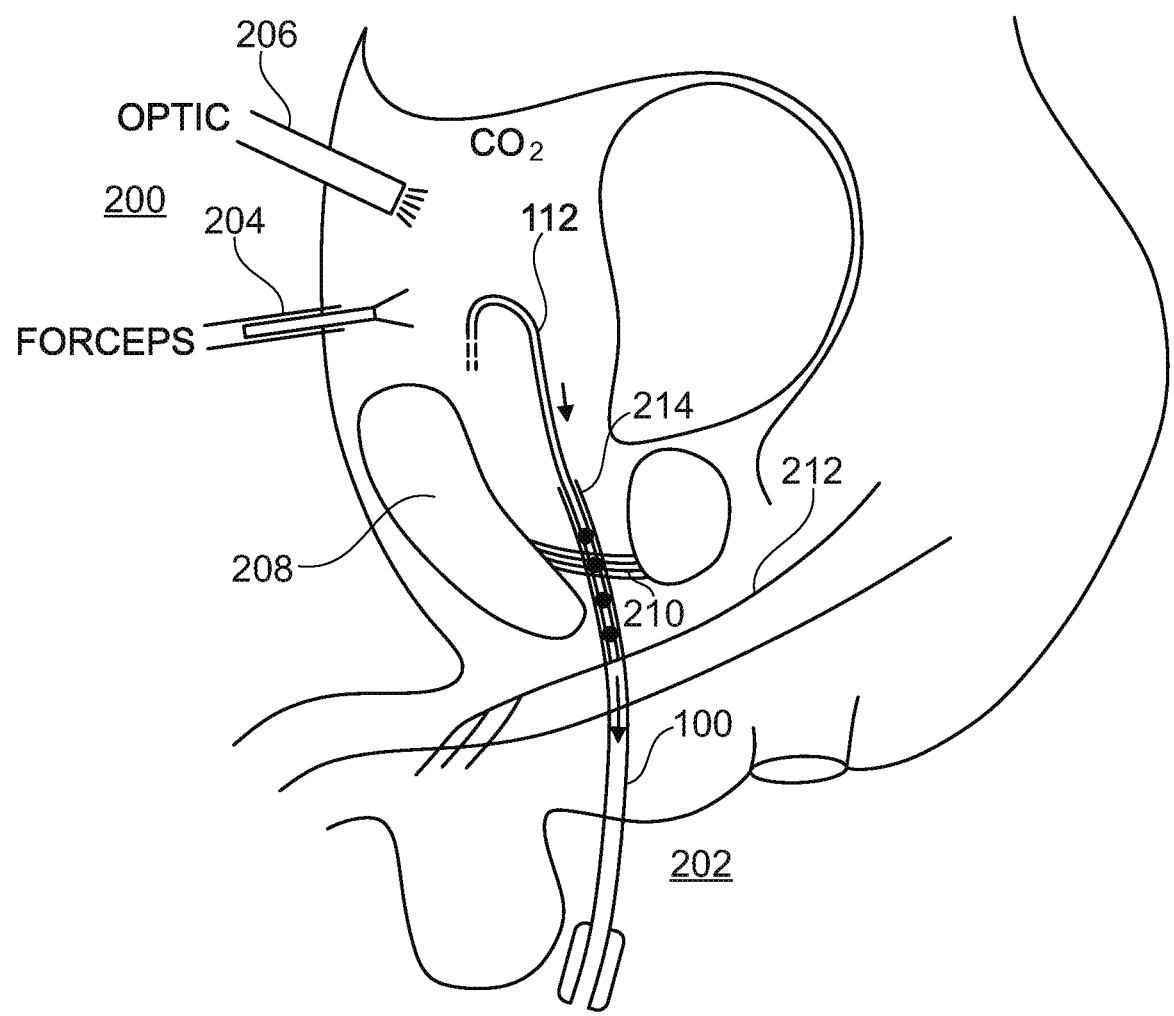

Referring next to FIG. 9, the next step of the process is illustrated, sharp tip 104 has now been completely removed, and an electrode 112 is introduced to the space endoscopically, again for example through a cannula with forceps 204. With the aid of optics 206, electrode 112 is guided to a now open end 214 of tool 100, and guided into tool 100, retrograde, into the hollow needle or tube which remains from tool 100.

Figure 10:
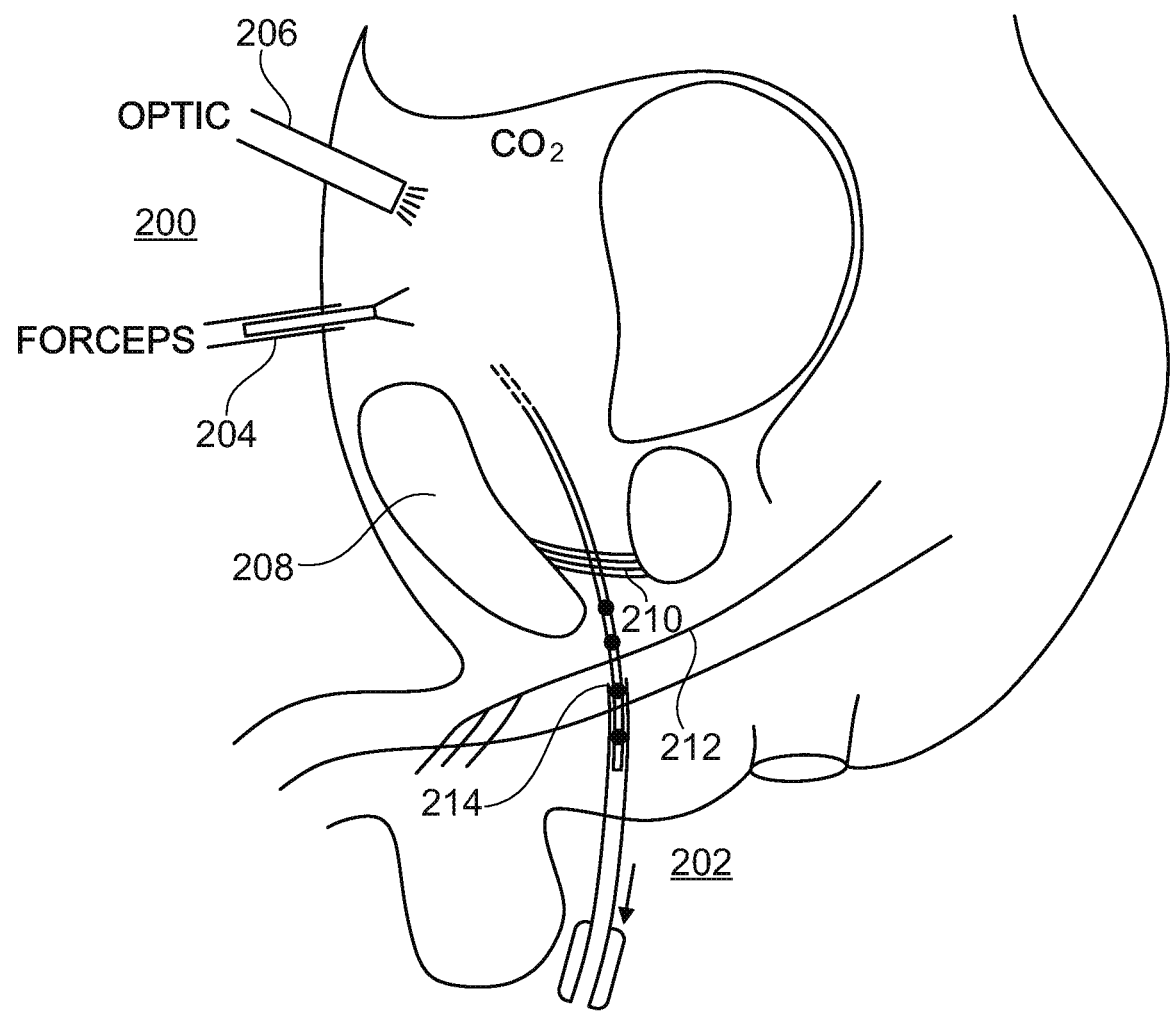

Referring next to FIG. 10, once electrode 112 is sufficiently fed into tool 100, tool 100 can be removed as shown in FIG. 10, leaving electrode 112 in place, in the correct location, and accessing nerve 212 as desired.

Figure 11:
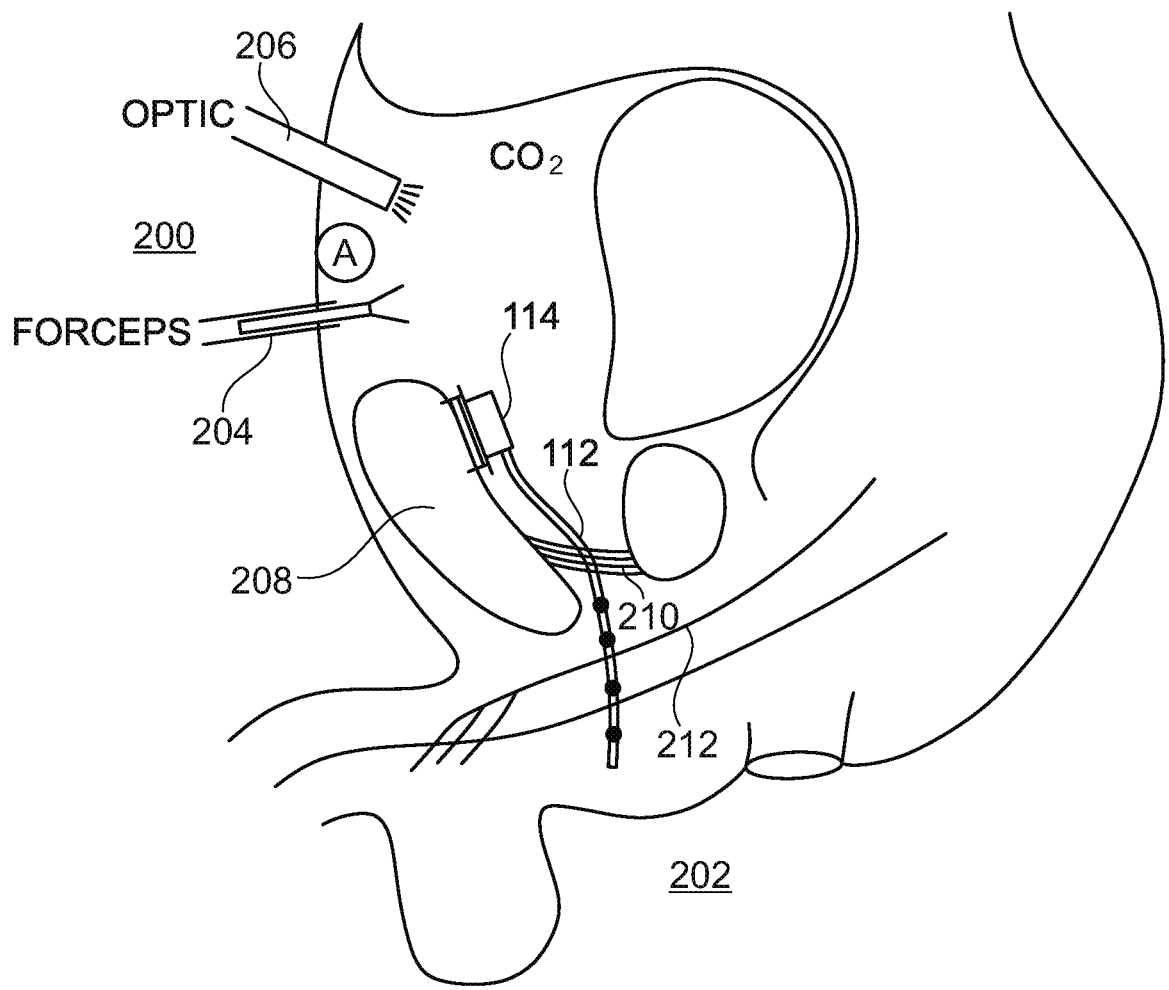

At this stage, the electrode 112 is in the proper position. If a generator or pacemaker is to be included in the implanted equipment, as shown for example at 114, generator 114 can also be fixed in place at this stage, for example by securing to the pubic bone 208 as shown in FIG. 11.

It should be appreciated that the unique combination of tool and steps as outlined in connection with FIGS. 7-11 allow for clear and direct visibility and accessibility to the Retzius space as well as nerves at or near the pelvic floor, such that a neurostimulator including electrode 112 and, optionally, a generator or pacemaker 114, can be safely and reliably implanted.

It should be appreciated that the presently disclosed process for implanting a neurostimulator can find desirable applicability for numerous different situations, including but not limited to those conditions, treatments and remedies and outlined above.

It should be appreciated that the present disclosure also utilizes tool 100 having sharp tip 104 in the form of a flexible shaft or cable which fit within a hollow space within tool 100. Thus, tool 100 can be a hollow tube with sharp tip 104 on a shaft disposed within the hollow tube and held against proximal movement relevant to the hollow tube so that the assembled tool 100, with sharp tip 104 can be used to enter the Retzius space through the pelvic floor as shown in FIG. 8, and also allowing removal of sharp tip 104 from tool 100 endoscopically through points of entry into the space of Retzius which have been accessed endoscopically, that is, from above the pelvic floor.

The process could of course be conducted using a tool configured differently with a sharp tip removable in a different manner. Nevertheless, a tool as disclosed herein has been found to be particularly useful in carrying out the process of the present invention.

This has the combined advantage of performing the implantation both from above and below the pelvis. The approach from below allows exact positioning of where the electrode is to be mounted, without the actual electrode or other components being introduced from the bottom area, where risk would be increased of infection or the like due to bacterial contamination of any tool introduced through the tube or shaft of tool 100. In the meantime, the approach from below is also performed under complete observation by the surgeon, from video devices positioned from the upper or top side. Further, once the sharp tip is removed and the generator implanted, images of the open tube, exposed by removal of the sharp tip, allow the neurostimulator and generator to be positioned exactly to the location of the target nerve or nerve plexus, from the upper or top side.

The invention claimed is:

1. A method for implanting a neurostimulator to a location within the pelvis of a patient, comprising the steps of:
    laparoscopically dissecting the Retzius space within the pelvis;
    positioning optics laparoscopically to view the Retzius space;
    positioning a curved needle along a path, having an open end and a removable tip mounted to the open end, into the Retzius space from below the pubic bone and until the removable tip is visible in the Retzius space through the optics;
    entering the Retzius space laparoscopically with a tool;
    removing the removable tip from the curved needle with the tool, and removing the tip from the Retzius space laparoscopically, wherein the tool is a laparoscopic manipulating tool, and wherein the step of removing the removable tip comprises grasping the removable tip with the laparoscopic manipulating tool, separating the removable tip from the open end of the curved needle, and withdrawing the laparoscopic manipulating tool and removable tip laparoscopically from the Retzius space;
    positioning the neurostimulator into the Retzius space laparoscopically into the open end along the path of the curved needle;

and removing the curved needle from the Retzius space along the path, leaving the neurostimulator in position along the path in the Retzius space.

2. The method of claim 1, wherein the removing step comprises removing the curved needle to leave the neurostimulator in place along the path, in contact with the cavernous and dorsal nerve of the patient.

3. The method of claim 2, further comprising the step of laparoscopically positioning a generator for the neurostimulator into the Retzius space and fixing the generator to the pubic bone.

4. The method of claim 1, wherein the step of positioning the curved needle comprises guiding the removable tip, while being observed with the optics, to the location where the neurostimulator is to be implanted.

5. The method of claim 1, wherein the laparoscopic manipulating tool and the removable tip are removed through a cannula extending laparoscopically into the Retzius space.

* * * * *